(12) United States Patent
Trodler

(10) Patent No.: US 8,156,934 B2
(45) Date of Patent: Apr. 17, 2012

(54) DEVICE FOR SECURING AIRWAY TUBING TO A PATIENT

(75) Inventor: Yakov Trodler, Lod (IL)

(73) Assignee: Trodek Ltd., Lod (IL)

( * ) Notice: Subject to any disclaimer, the term of this patent is extended or adjusted under 35 U.S.C. 154(b) by 689 days.

(21) Appl. No.: 12/067,459

(22) PCT Filed: Sep. 21, 2006

(86) PCT No.: PCT/IL2006/001116
§ 371 (c)(1),
(2), (4) Date: Mar. 20, 2008

(87) PCT Pub. No.: WO2007/034493
PCT Pub. Date: Mar. 29, 2007

(65) Prior Publication Data
US 2008/0210232 A1    Sep. 4, 2008

(51) Int. Cl.
A62B 9/04    (2006.01)
(52) U.S. Cl. .......... 128/202.27; 128/200.26; 128/207.14
(58) Field of Classification Search ............. 128/200.26, 128/205.25, 201.24, 200.24, 202.27, 206.21, 128/206.29, 207.11, 207.14, 207.17, 207.15; 403/348–353; 285/322, 324, 314, 243; 24/16 R, 24/19, 268
See application file for complete search history.

(56) References Cited

U.S. PATENT DOCUMENTS

| | | | |
|---|---|---|---|
| 2,127,215 A | 8/1938 | Gwathmey | |
| 2,693,182 A | 11/1954 | Phillips | |
| 3,616,799 A | 11/1971 | Sparks | |
| 3,927,799 A | 12/1975 | Tindley | |
| 4,067,331 A | 1/1978 | Berman | |
| 4,090,518 A | 5/1978 | Elam | |
| 4,235,229 A | 11/1980 | Ranford et al. | |
| 4,270,529 A | 6/1981 | Muto | |
| 4,270,778 A * | 6/1981 | Brownell | 285/305 |
| 4,304,228 A | 12/1981 | Depel | |
| 4,326,515 A | 4/1982 | Shaffer | |
| 4,328,979 A * | 5/1982 | Stoll | 285/148.14 |
| 4,414,973 A * | 11/1983 | Matheson et al. | 128/206.15 |
| 4,683,882 A | 8/1987 | Laird | |
| 4,744,358 A | 5/1988 | McGinnis | |
| 4,906,234 A | 3/1990 | Voychehovski | |
| 5,009,227 A | 4/1991 | Nieuwstad | |
| 5,026,352 A | 6/1991 | Anderson | |
| 5,123,410 A | 6/1992 | Greene et al. | |
| 5,146,913 A | 9/1992 | Khorsandian | |
| 5,251,616 A | 10/1993 | Desch | |

(Continued)

FOREIGN PATENT DOCUMENTS
WO    95/08356    3/1995
(Continued)

*Primary Examiner* — Justine Yu
*Assistant Examiner* — Colin W Stuart
(74) *Attorney, Agent, or Firm* — Faegre Baker Daniels LLP

(57) ABSTRACT

An airway tube securing device (ASTD) having a tubular constrictor attached to an oral piece and a fastener for fastening the ASTD to the face of a patient provides for the correct placing and fixation of an airway tube within the patient's airways. A rotatable clamp provides for constricting the airway tube thereby securing it to the oral piece. An optional mouthpiece attached to the proximal face of the oral piece provides for the protection of the tube from the jaws of a patient. One or two apertures in the oral piece provide for further insertion of tubing, auxiliary intubation tools and or probes.

18 Claims, 4 Drawing Sheets

U.S. PATENT DOCUMENTS

| | | | |
|---|---|---|---|
| 5,345,931 A | | 9/1994 | Battaglia, Jr. |
| 5,419,319 A | | 5/1995 | Werner |
| 5,513,633 A | * | 5/1996 | Islava ........................ 128/207.17 |
| 5,555,881 A | | 9/1996 | Rogers et al. |
| 5,626,128 A | | 5/1997 | Bradley et al. |
| 5,653,232 A | | 8/1997 | Rogers et al. |
| 5,720,759 A | | 2/1998 | Green et al. |
| 5,746,202 A | | 5/1998 | Pagan |
| 5,803,079 A | | 9/1998 | Rogers et al. |
| 6,036,237 A | * | 3/2000 | Sweeney ........................ 285/322 |
| RE36,702 E | | 5/2000 | Green et al. |
| 6,067,985 A | | 5/2000 | Islava |
| 6,257,238 B1 | * | 7/2001 | Meah ........................... 128/859 |
| 6,517,549 B1 | * | 2/2003 | Dennis ......................... 606/108 |
| 6,578,576 B1 | | 6/2003 | Taormina et al. |
| 6,634,359 B1 | | 10/2003 | Rudy, Jr. et al. |
| 6,688,306 B1 | | 2/2004 | Cise et al. |
| 6,755,191 B2 | * | 6/2004 | Bertoch et al. ............ 128/200.26 |
| 7,353,822 B2 | | 4/2008 | van Hooser et al. |
| 7,866,314 B2 | | 1/2011 | Isenberg et al. |
| 2002/0108609 A1 | * | 8/2002 | Elkins ...................... 128/200.24 |
| 2007/0006878 A1 | * | 1/2007 | Mackey et al. .......... 128/200.26 |
| 2007/0066460 A1 | * | 3/2007 | Torres ........................... 482/124 |
| 2010/0095968 A1 | | 4/2010 | Ogilvie et al. |

FOREIGN PATENT DOCUMENTS

| | | |
|---|---|---|
| WO | 2010/033109 | 3/2010 |

\* cited by examiner

DEVICE FOR SECURING AIRWAY TUBING TO A PATIENT

FIELD OF THE INVENTION

The present invention relates to auxiliary tools for securing airway tubing to a patient.

BACKGROUND OF THE INVENTION

Oral intubation is commonly applied in the course of medical treatments such as operations involving anesthesia, in which breathing is assisted and controlled by airway tubing. Endotracheal and/or laryngeal tubes are typically used in such operations for delivering oxygen and medicines to the trachea. The correct placement and fixation of such tubes is critical in maintaining the patient's wellbeing. Commercially available laryngeal masks in various configurations, provide for proper tubing fixation. However, displacement of the tubing remains a risk. Even initially as an endotracheal tube is properly positioned and secured by currently available means, the tube will often displace due to mechanical activity, associated with the instrumentation and patient movements. Such displacement can harm the patient in several ways. Effort invested in the development of superior intubation means, yielded auxiliary intubation tools, aids and procedures. Securing the insertion of endotracheal tubes still require attention of the medical team which interfere with other essential procedures. A device disclosed in U.S. Pat. No. 5,626,128 addresses this problem by maintaining an endotracheal tube in proper position within a patient's mouth by means of an oral adhesive composition. However, the employment of such a device obviates the use of some additional devices targeted at the oral cavity, such as suction tubes.

DESCRIPTION OF THE PRESENT INVENTION

Figure 1:
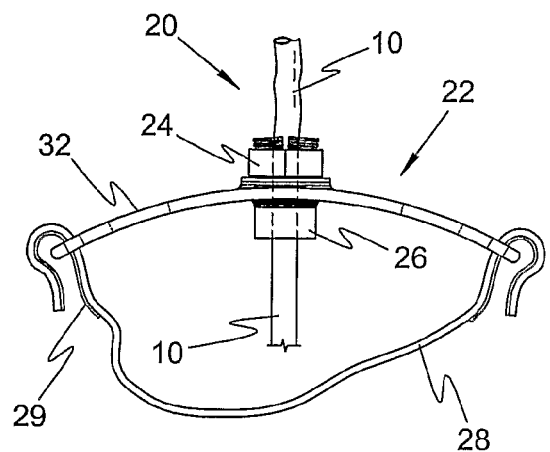
FIG. 1 is a side view of a preferred embodiment of the airway tube securing device (ATSD) according to the present invention.

Reference is first made to FIG. 1, which schematically shows a side view of an airway tube securing device (ATSD), according to a preferred embodiment of the present invention. A section of airway tube 10 is shown traversing a pass-through aperture in segmented constrictor 20 of oral piece 22. By rotating clamping means 24 the inner diameter of the segmented constrictor diminishes, thereby clumping airway tube 10 and securing it firmly to oral piece 22. Mouthpiece 26 substantially coaxial with airway tube 10 protrudes from the proximal face of oral piece 22. The mouthpiece is inserted in a patient's oral cavity between upper and lower jaws. Face fastening strip 28 with Velcro® strips 29 attached to both ends, respectively, fastens the oral piece to the patient's face by strapping fastening strip 28 against the patient's neck onto either its proximal or distal faces. Other variants of the fastening mechanism include different connecting means, used to connect strips 29 to oral piece 22, including among other possibilities buckles, clamping connectors, hooks attached to the strips' ends, or Velcro® strips attached to the proximal face of the fastening strip.

Figure 2:
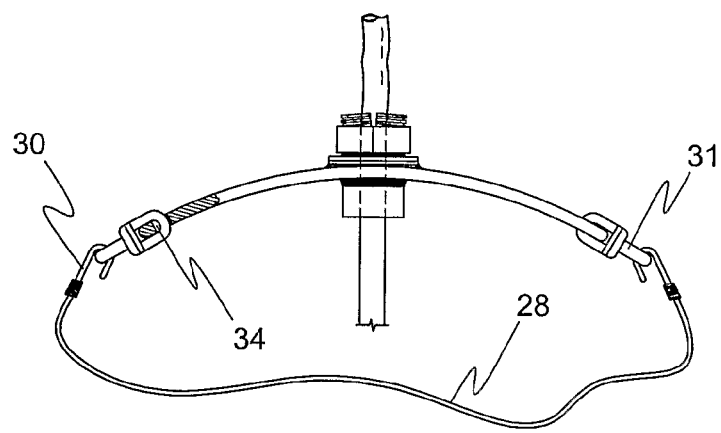
FIG. 2 is a side view of the ATSD shown in FIG. 1, with an elastic facial fastening strip.

Reference is now made to FIG. 2, showing an oral piece of the invention, implementing an elastic facial fastening strip, using hook 30 inserted into ring 31 connected to the oral piece end by means of strip connector aperture. Strip hooks may also be directly inserted into strip connector apertures. Hook 30 attached at the end of the fastening strip is shown passing through strip connector apertures 34.

Figure 3:
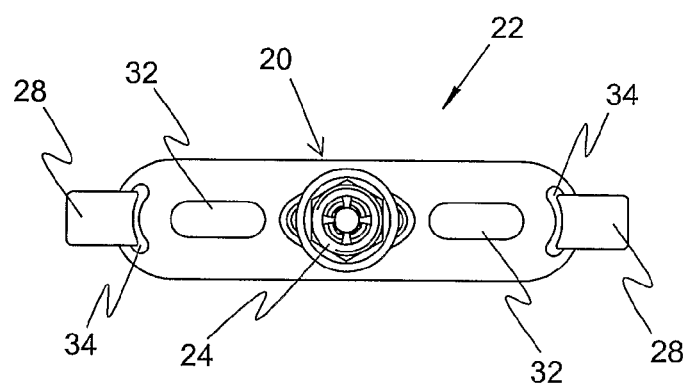
FIG. 3 is a top side view of the ATSD shown in FIG. 1.

Reference is made to FIG. 3 showing a topside view of an ATSD of the invention. Segmented constrictor 20 is located at the center of oral piece 22. Two additional apertures 32, adjacent segmented constrictor 20 and distributed symmetrically at its sides, facilitate the application of additional devices such as thermometers, probes and/or suction tubes. The ends of fastening strip 28 are shown passing through strip connector apertures 34 symmetrically located on both sides of the oral piece.

Figure 4:
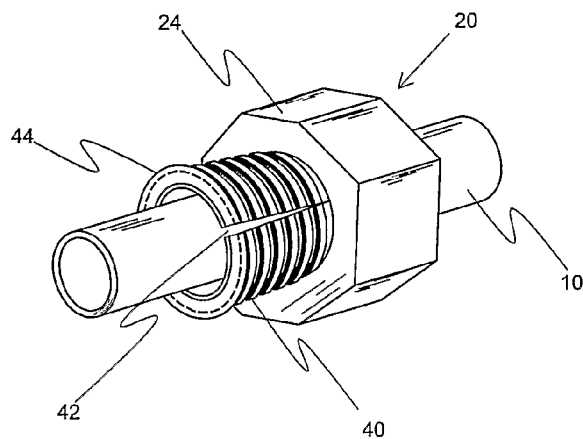
FIG. 4 is an isometric view of a preferred embodiment of the constrictor according to the present invention.

Reference is made to FIG. 4 showing an isometric view of segmented constrictor 20, in which airway tube 10 is inserted. Set of constricting segments 40, having a cylindrical thread on their external surfaces and a conic interior (not shown) is split by longitudinal section 42 into two segments. One end of each of the constricting segments is firmly secured to the oral piece. The internal surface of constricting segments 40 is roughened for higher friction and improved clamping of the airway tube. The radius of the lumen of segmented constrictor 20 decreases as the distance from the distal face of the oral piece increases. Insertion of an airway tube into segmented constrictor 20 divides the longitudinal constricting segments 40 along longitudinal section 42. Segmented constrictor 20 according to the invention also consists of a clamping means that is a hollow body such as a nut, rotatable over the constricting segments such that the pressing force exerted over the constricting segments increases or decreases according to its direction of rotation. Rotating clamping means 24 clockwise changes the inner diameter of the segmented constrictor due to its interior conical shape. Decreasing the inner diameter of segmented constrictor 20 applies pressure to the exterior surface of airway tube 10 pressing it against the constricting segments. Flexible ring 44 attached to one or both ends of the segmented constrictor wall 40 prevents clamping means 24 from falling off.

By means of properly selecting internal conical shape and angle formed by the inner surface of the constricting segments and external thread spacing, the same segmented constrictor can be adapted to a range of tube diameters starting with one of 2.5 millimeters (mm) suitable for neonates and up to 10-11 mm for male adults. Rotating the constrictor nut by a specific rotational angle changes the inner diameter of the segmented constrictor proportionally. One segmented constrictor may be adapted to cover the entire range of available airway tubes.

Securing the airway tube to the oral piece is typically achieved at a point in which tightening the segmented constrictor nut requires a significantly higher rotational torque. An experienced operator is capable of securing the airway tube fixed to the oral piece by sense of touch. It is possible to ensure that the suitable rotational angle of the nut for loosening or tight clamping of a specified airway tube is easily recognised by the medical team. One way, for example, is to configure the segmented constrictor such that rotating the constrictor nut by 90° is equivalent to a 0.5 mm change in the diameter of the airway tube. Alternatively, it is possible to apply colour to the thread coils accordingly, employing different hues for designating the progression of the constricting nut on the thread. Namely, threads coils corresponding to tube diameter below 3 mm are coloured with black, the range 3-4 mm with deep red, 4-5 light red, 5-6 orange, 6-7 yellow, 7-8 green 8-9 blue, 9-10 violet and above 10 white. Other variants consist of a few dedicated oral pieces having segmented constrictors corresponding to different ranges of airway tube diameters and further employing colour coding corresponding to these different ranges, in a similar scheme as described above.

In another embodiment of the present invention, a knob is employed, such that distinctly audible clicking sounds indicate a proper alignment with the inserted tube. The knob is installed at the segmented constrictor side extending sideways at the distal side of the oral piece. The knob is coupled to the constrictor nut by means of an axle. Click indications correspond to the following tube diameter values: 2.5, 3, 3.5, and 4 mm.

Figure 5A:
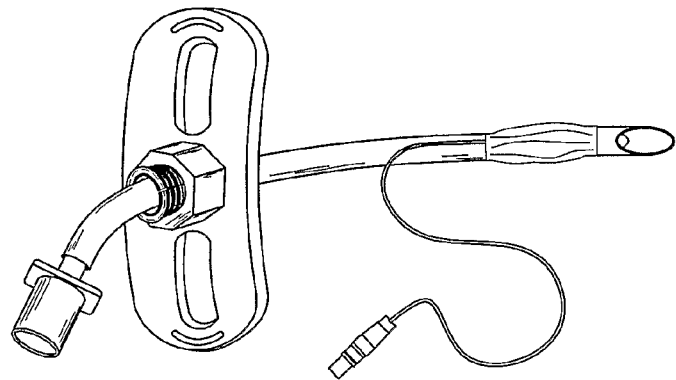
FIG. 5A is an isometric view of an ATSD according to the present invention, attached to a Murphy cuffed endotracheal tube.
Figure 5B:
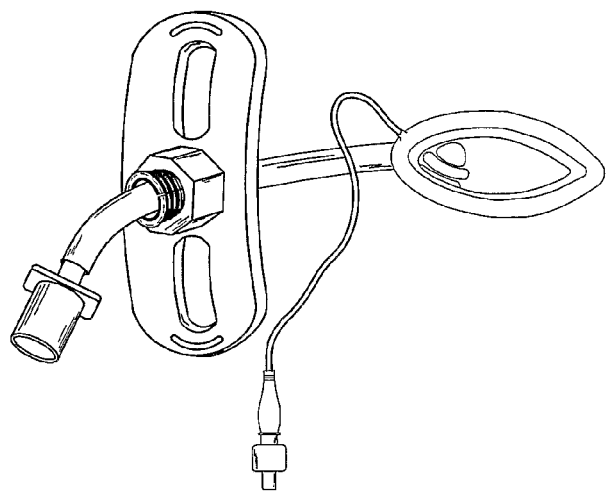
FIG. 5B is an isometric view of an ATSD according to the present invention, attached to a laryngeal mask.

The ATSD in accordance with the present invention is typically made of plastic material that can sustain high temperatures. Such an ATSD can be sterilized and reused, thus providing an inexpensive and valuable intubation aid to be used in the operation theatre. The ATSD is accommodated for attaching various laryngeal as well as endotracheal airway tubes in place. Reference is made to FIGS. 5A-B. In FIG. 5A an ATSD applied to a Murphy cuffed endotracheal tube is shown. In FIG. 5B an ATSD as applied to a laryngeal mask is shown. A suitable ATSD may be packaged separately or together with a respective endotracheal airway tube, or with a laryngeal mask, as an airway intubation kit, ready for use by the medical staff.

Figure 6A:
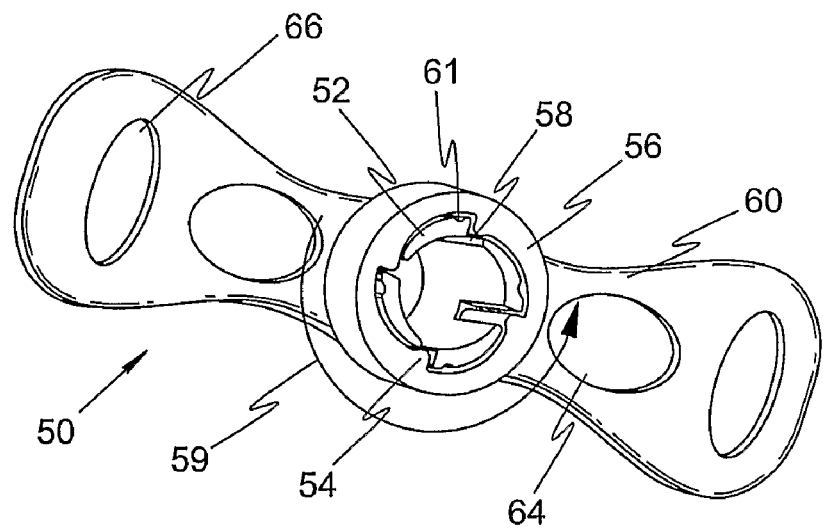
FIG. 6A is an isometric view of an ATSD according to another preferred embodiment of the present invention.
Figure 6B:
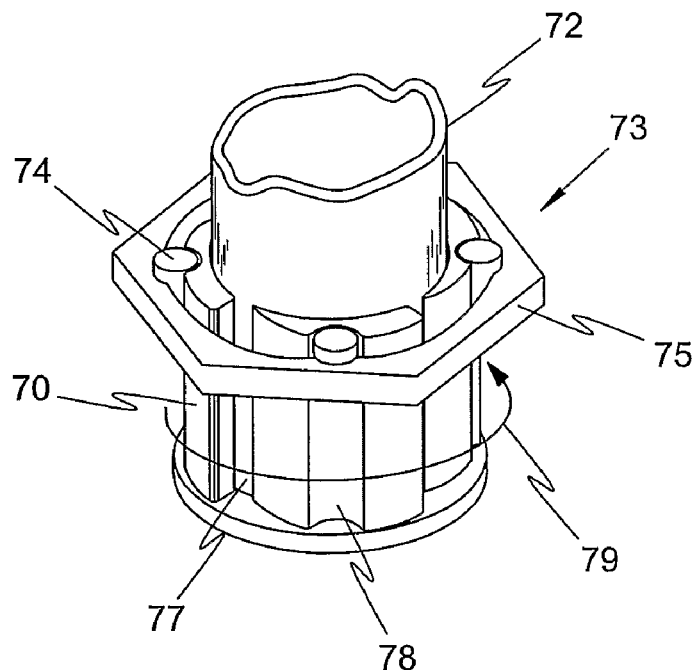
FIG. 6B is a sectional view of a constrictor according to a preferred embodiment of the present invention.

Reference is made to FIG. 6A-6B. In FIG. 6A an ATSD according to another preferred embodiment of the invention is shown. ATSD 50 consists of a longitudinally segmented tube the wall of which is divided into set of constricting segments 52. Each constricting segment has tapering flank. ATSD 50 is shown open, or unconstricted, in which state inwardly protruding projections 54 located on the inner surface of annular clamping means 56 are projected into corresponding recesses 58 spacing constricting segments 52 apart. The airway tube, not shown, is securely locked inside oral piece 60 by rotating clamping means 56 in the direction indicated by arrow 59. By such rotation, projections 54 force segments 52 against the exterior surface of the airway tube. Clamping means 56 is securely locked in a constricting position, when projections 54 reach corresponding recesses 61. The airway tube is unlocked by rotating clamping means 56 in the opposite direction. Oral piece 60 has one or two additional apertures 64 for the optional insertion of additional devices and or tubes as described hereinbefore. Apertures 66 provide for connecting a fastening strip to oral piece 60. Oral piece 60 has the option for a mouthpiece attachment to its proximal face, providing for protection of the tubers from the patient's jaws. In FIG. 6B a sectional view of a segmented constrictor according to another embodiment of the present invention is shown in a constricting position. Constricting segments 70 compress airway tube 72 as pawls 74 of annular clamping means 75 press them against the wall of airway tube 72. By such pressing the lumen of segmented constrictor 73 becomes partially conic as its diameter decreases along the flanks of the constricting segments as the distance from the distal face of the oral piece increases. Segmented constrictor 73 attains a secure constricting position as pawls 74 are shifted from the longitudinal slits 77 into is external recesses 78 in the constricting segments by rotating clamping means 75 having internal recesses for securing the pawls in the direction indicated by arrow 79.

Figure 7:
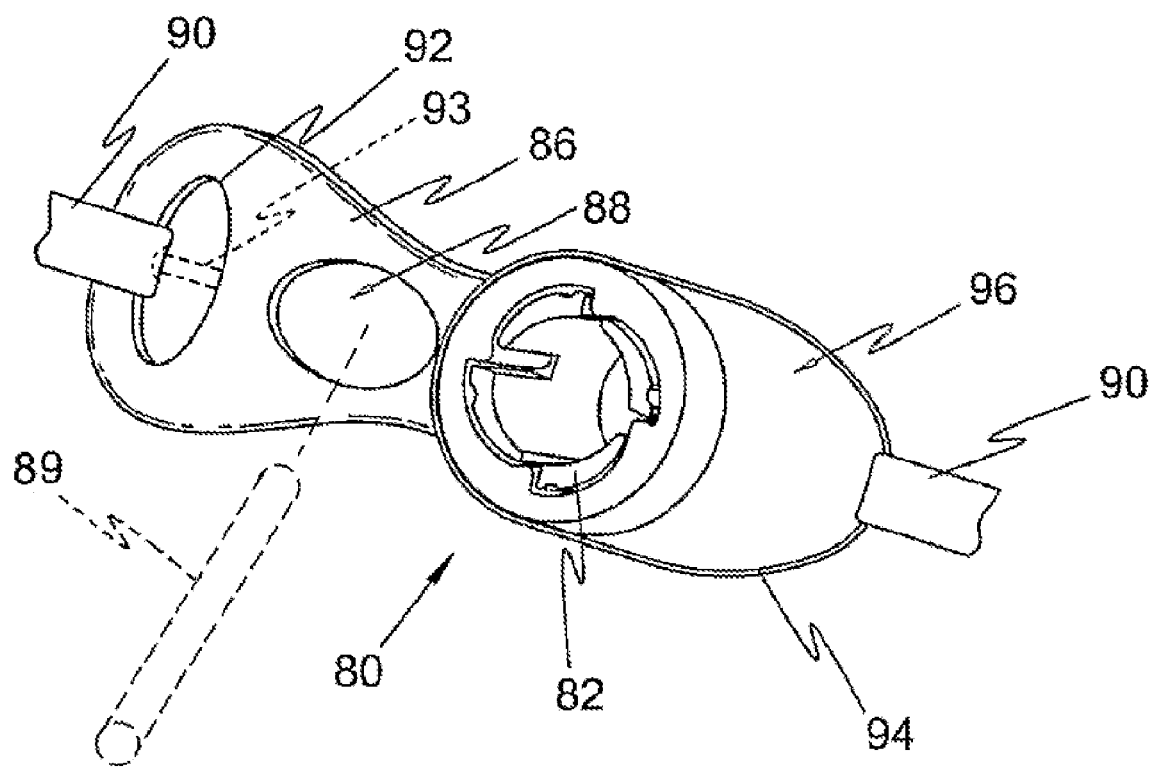
FIG. 7 is an isometric view of an ATSD according to another preferred embodiment of the present invention.

Reference is now made to FIG. 7 in which an ATSD according to another preferred embodiment is shown. This ATSD consists of the same segmented constrictor 80 as the ATSD shown in FIG. 6A. The oral piece of this ATSD has only one side 86 having optional aperture 88. This aperture 88 provides for the insertion of additional devices 89 (shown in phantom), where each device 89 may be in the form of a thermometer, an ultrasound probe, or a suction tube, for example. Fastening strip 90 is connected to corresponding aperture 92 located at the end of oral piece 86. Optionally, oral piece 86 includes a buckle 93 (shown in phantom) for connecting the ATSD to fastening strip 90. Noose 94 attached to the other end of fastening strip 90 is hooked to segmented constrictor 80 such that a space 96 is made available for the insertion of additional devices and/or probes (such as an ultrasound probe) into a patient's oral cavity.

The invention claimed is:

1. A device for securing an airway tube in an airway of a patient, comprising:
   an oral piece connectable to said patient;
   at least one pass-through aperture formed in said oral piece for inserting an airway tube in said patient's airway through said oral piece;
   a longitudinally segmented constrictor secured to said oral piece, said segments of said constrictor defining a lumen that is continuous with said aperture of said oral piece to receive said airway tube; and
   an annular clamp rotatable over said constrictor, wherein said segments of said constrictor are compressible by said clamp,
   wherein said segments of said constrictor define external longitudinal recesses to retain pawls which are also retained by respective recesses in said clamp, said pawls forcing said segments of said constrictor together to secure said constrictor in a constricting position.

2. The device of claim 1, wherein said oral piece includes a proximal face that faces said patient, the device further comprising a mouthpiece protruding from said proximal face of said oral piece for protecting said airway tube from the jaws of said patient.

3. The device of claim 1, wherein said oral piece has two or more pass-through apertures.

4. The device of claim 1, wherein said segments of said constrictor have a roughened internal surface.

5. The device of claim 1, further comprising a face fastening strip for connecting said oral piece to said patient, wherein said face fastening strip is longitudinally elastic.

6. The device of claim 5, wherein said face fastening strip is connected to said oral piece by means of hooks inserted into connector apertures located at both ends of said oral piece.

7. The device of claim 5, wherein said face fastening strip is connected to said oral piece by means of hooks inserted into rings attached at both ends of said oral piece.

8. The device of claim 5, further comprising a buckle that connects said oral piece to one end of said face fastening strip.

9. The device of claim 3, wherein said pass-through apertures are sized to receive at least one of a thermometer, an ultrasound probe, and a suction tube.

10. The device of claim 1, wherein said clamp includes inwardly protruding projections that force said segments of said constrictor together to secure said constrictor in a constricting position.

11. A device for securing an airway tube in an airway of a patient, comprising:
   an oral piece connectable to said patient;
   a constrictor coupled to said oral piece, said constrictor having a plurality of segments that cooperate to define an aperture for receiving said airway tube, said constrictor having a first configuration in which said segments are forced inwardly to narrow said aperture and a second configuration in which said segments are released outwardly to widen said aperture; and
   a clamp moveably coupled to said constrictor to adjust said constrictor between said first configuration and said second configuration,
   wherein said clamp includes a plurality of inwardly protruding projections, said projections abutting said segments of said constrictor in said first configuration to force said segments inwardly, and said projections aligned substantially between adjacent segments of said constrictor in said second configuration to allow said segments to move outwardly.

12. The device of claim 11, wherein said clamp is externally coupled to said constrictor to at least partially surround said constrictor.

13. The device of claim 11, wherein said clamp is rotatably coupled to said constrictor.

14. The device of claim 11, wherein said aperture of said constrictor is adjustable from a first diameter of about 2.5 millimeters to a second diameter between about 10 and 11 millimeters.

15. A method for securing an airway tube in an airway of a patient, the method comprising the steps of:
   providing a device that includes an oral piece, a constrictor coupled to said oral piece, said constrictor having a plurality of segments that cooperate to define an aperture, and a clamp;
   securing said oral piece to said patient;
   inserting said airway tube into said aperture of said constrictor; and
   moving said clamp relative to said constrictor to tighten said segments against said airway tube,
   wherein said clamp includes a plurality of inwardly protruding projections, said projections abutting said segments of said constrictor in a first configuration to force said segments inwardly, and said projections aligned substantially between adjacent segments of said constrictor in a second configuration to allow said segments to move outwardly.

16. The method of claim 15, wherein said oral piece includes a first aperture that communicates with said aperture of said constrictor to receive said airway tube and a second aperture that is spaced apart from said first aperture, the method further including the step of inserting one of a thermometer, a probe, and a suction tube through said second aperture of said oral piece.

17. A device for securing an airway tube in an airway of a patient, comprising:
   an oral piece connectable to said patient;
   a constrictor extending longitudinally from said oral piece, said constrictor comprising a plurality of segments that are radially-spaced apart, said plurality of segments cooperating to define an aperture for receiving said airway tube;
   a clamp rotatably coupled to said constrictor to adjust said constrictor between a first configuration and a second configuration, said clamp comprising a plurality of projections that are radially-spaced apart and that protrude inwardly toward said constrictor, said projections abutting said segments of said constrictor in said first configuration to force said segments inwardly toward said airway tube, said projections aligned substantially between adjacent segments of said constrictor in said second configuration to allow said segments to move outwardly away from said airway tube.

18. The device of claim 17, wherein each of said segments defines an outwardly-facing recess that receives a corresponding one of said projections in said first configuration.

\* \* \* \* \*